United States Patent [19]

Turner

[11] 4,001,142

[45] Jan. 4, 1977

[54] BLOOD GAS CONTROL

[75] Inventor: James E. Turner, Madison, N.J.

[73] Assignee: Warner-Lambert Company, Morris Plains, N.J.

[22] Filed: July 25, 1975

[21] Appl. No.: 599,291

[52] U.S. Cl. .............................. 252/408; 23/230 B
[51] Int. Cl.² ................. G01N 31/00; G01N 33/16
[58] Field of Search .............. 252/408 R; 23/230 B

[56] References Cited

UNITED STATES PATENTS

| 2,937,146 | 5/1960 | Cutlip et al. | 252/75 |
| 3,380,929 | 4/1968 | Petersen | 252/408 |
| 3,466,249 | 9/1969 | Anderson | 23/230 B |
| 3,681,255 | 8/1972 | Wilfore | 252/408 |
| 3,859,049 | 1/1975 | Ware et al. | 252/408 |

*Primary Examiner*—Leland A. Sebastian
*Attorney, Agent, or Firm*—Albert H. Graddis; Frank S. Chow; George M. Yahwak

[57] ABSTRACT

Disclosed are a stable, non-protein, buffered control material for monitoring the reliability of blood gas instruments in the acid, normal, and alkaline ranges.

16 Claims, No Drawings

BLOOD GAS CONTROL

Improvements in instrumentation have made the determination of blood pH, $P_{O_2}$, and $P_{CO_2}$ increasingly available to the medical technologist. Since vigorous therapeutic treatment is often dictated by test results, accuracy is essential. Accordingly, the use of control materials to verify the reliability of instrumentation and to provide an immediate indication of unexpected analytical deviations is important.

In the past, control materials to verify the reliability of blood pH, $P_{O_2}$, and $P_{CO_2}$ instruments had to be made by the medical technologist immediately prior to performing the test functions. Generally, this involves the adding of known quantities of oxygen and carbon dioxide gases to a Tonometer which contains a control sample liquid at a fixed pH. The gases and the liquid are equilibrated, within the Tonometer, and an aliquot sample is removed carefully by the technician for controlling the blood gas instrumentation. As a result of the meticulous work involved and the necessity of specific gas mixtures, this has only been performed previously in laboratories conducting research in the blood gas field.

Other methods of assessing the instrument function do not test all of the blood gas parameters. For example, Versatol Acid-Base (sold by the General Diagnostics Division of Warner-Lambert Company), derived from human blood and especially designed to simulate a serum sample is used to control the blood gas measurements of pH and $P_{CO_2}$. This is a lyophilized product, however, and it not only requires reconstitution of material, but also is not capable of testing the $P_{O_2}$ function of the instrument.

Stability has also been lacking in prior control materials. Exposure to air immediately begins to effect $P_{O_2}$ and $P_{CO_2}$ values. Clinical control materials containing protein are subject to bacterial contamination which causes immediate lowering of $P_{O_2}$ values and increases $P_{CO_2}$ values.

I have now developed a packaged and convenient trilevel control system for monitoring laboratory measurement of pH, $P_{O_2}$, and $P_{CO_2}$ with blood gas analyzing instruments. The three controls, in ready to use liquid form, are formulated to simulate physiological levels over the clinically significant range of acid base respiratory balance and function. When used together, they provide a simple, reliable, full range quality control set and confirm the calibration and performance characteristics of blood gas instrumentation.

Accordingly, the object of this invention is to prepare a novel, stable, aqueous solution possessing chemically significant values for pH, partial pressure of oxygen ($P_{O_2}$), partial pressure of carbon dioxide ($P_{CO_2}$) and bicarbonte concentration [$HCO_3^-$] to be used as a control for monitoring instruments that measure these parameters.

In simplest terms, what is disclosed is a satisfactory, color coded liquid control for pH, $P_{O_2}$, and $P_{CO_2}$ at three levels (alkalosis, acidosis, normal) free of all proteins. The final heat sterilized product contains a suitable dye, triethanolamine-acetic acid buffer, and sodium bicarbonate in equilibrium with a controlled atmosphere of oxygen, carbon dioxide and nitrogen.

In preliminary experiments, liquid blood gas controls were also prepared from blood serum as was the lyophilized Versatol Acid-Base. These controls presented many problems particularly relating to long term stability since it was difficult to obtain a sterile material. Since many of the microorganisms contaminating the sera were aerobes, as soon as the condition of the control became optimal for bacterial growth, the microorganisms immediately began to metabolize the gaseous oxygen and to produce carbon dioxide which rendered the control useless. It therefore became necessary to sterilize the final product and because of the presence of serum proteins, the use of heat sterilization was precluded. It therefore was necessary to use chemical preservatives to maintain sterility. The liquid gas control of the present invention does not contain serum proteins and therefore may be sterilized in an autoclave without affecting the composition of the material. This thereby eliminates any problems which might be encountered by adding chemical preservatives to the control material.

The pH, $P_{CO_2}$, and bicarbonate concentration of a solution are interrelated according to a well defined chemical equilibrium expressed mathematically by the Henderson-Hasselbalch equation. Therefore, the desired control values for pH and $P_{CO_2}$ were obtained by estimating, with the aid of the Henderson-Hasselbalch equation, the necessary starting pH and bicarbonate concentration that would provide the correct final values following complete equilibration with the atmosphere in contact with the solution.

The desired $P_{O_2}$ values were obtained more simply than the $P_{CO_2}$ values, since oxygen, unlike carbon dioxide, does not take part in a chemical reaction in the liquid base. The only factor governing the $P_{O_2}$ of the control solution is the quantity of oxygen physically dissolved in the liquid phase which depends primarily on the partial pressure of oxygen in the gas phase; the partial pressure in turn is directly proportional to the amount of oxygen in the gas mixture. Therefore, the $P_{O_2}$ values are regulated by varying the percentage of oxygen in the equilibration gas mixture.

The pH and $P_{CO_2}$ parameters behave in much the same way in the control as in whole blood. They exhibit these similarities because they are regulated in both whole blood and the liquid control by the same reactions as shown below:

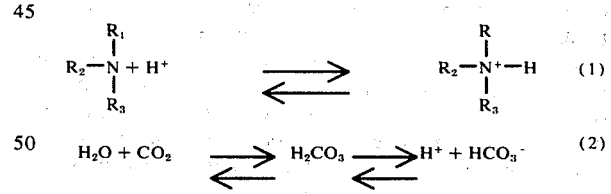

In whole blood the basic amino groups (equation No. 1) are composed of terminal and side chain amino groups of serum proteins and hemoglobin, whereas in the blood gas control they are furnished by triethanolamine. The pH buffering effect, however, is essentially the same in both cases. In addition to the pH, the $P_{CO_2}$, which is directly related to the $CO_2$ concentration, is buffered in both the control and whole blood by the reaction shown in equation 2. Therefore, the pH and $P_{CO_2}$ behave similarly in both due to the buffering effect of these two reactions.

The triethanolamine buffering system, in fact, mimics the whole blood pH curve with respect to temperature changes. As the temperature of whole blood increases over a range of 25° – 40° C, for example, the pH of the whole blood also increases along a given slope. The triethanolamine buffering system of this invention also causes the pH of the liquid control to increase along a similar slope. Thus as the temperature varies, the pH of whole blood and the liquid control will very in like manner.

The $P_{O_2}$, on the other hand, is not maintained in the aqueous control in exactly the same way that it is maintained in whole blood. Molecular oxygen in whole blood is in two forms — free and bound. The free form, which is actually dissolved in the aqueous phase, is in equilibrium with that bound to hemoglobin as shown in equation No. 3.

$$Hb + 4O_2 \rightleftarrows Hb[O_2]_4$$

The equilibrium of this reaction is such that the ratio of free to bound oxygen is approximately 1 to 35. In other words, the amount of free oxygen is small compared to the reservoir of bound oxygen. Since the $P_{O_2}$ is governed by the free oxygen concentration, the reservoir of bound oxygen in equilibrium with the free oxygen provides a high degree of oxygen buffering capacity in whole blood. In the case of the liquid blood gas control only free, dissolved oxygen is present. There is no bound oxygen. Therefore, since the concentration of dissolved oxygen is very small, the oxygen buffering capacity of the control is small compared with that of whole blood. There is, however, a different type of oxygen reservoir in the blood gas control ampul. The space above the liquid is occupied by a controlled atmosphere of oxygen, carbon dioxide and nitrogen, and the total quantity of oxygen in this space is approximately 40 times the quantity dissolved in the solution. This reservoir of oxygen gas serves two purposes. It establishes and maintains the desired $P_{O_2}$ in the solution as long as the ampul remains sealed and it provides a certain degree of buffering against atmospheric gases after the ampul has been opened. However, it does not provide sufficient oxygen buffering capacity in the solution to cause the control to mimic the exact $P_{O_2}$ behavior of whole blood, particularly the effect of temperature variation on $P_{O_2}$. For this reason, the control should be stored at room temperature or allowed to completely equilibrate at room temperature before use. It should be emphasized, however, that the lack of oxygen buffering capacity does not lessen the utility of the blood gas control in detecting faulty instrumentation or poor laboratory technique. On the contrary, it may actually enhance its utility. It is more sensitive than whole blood to external factors tht effect the $P_{O_2}$, such as, leaks in the chamber, improper bath temperature and exposure of the sample to the atmosphere.

The liquid blood gas control of this invention is thus designed to react in like manner as blood. Whatever parameters may effect whole blood readings in the blood gas instrument, will also effect similar changes in the control. If a human error or mechanical error exists which effects the pH, $P_{O_2}$, or $P_{CO_2}$ of the blood, that error will also effect the blood gas control since both systems are the same. Another problem that was encountered in the development of the liquid blood gas control of this invention was the instability of certain dyes on exposure to direct sunlight. This was particularly true of several blue and red dyes tested for use in the alkalosis and acidosis controls. The instability of the dye was also accompanied by a decrease in the $P_{O_2}$ value. Apparently a light catalyzed oxidation was occurring which did not take place at a detectable rate in the dark. This problem was solved by the careful selection of suitable dyes for all three control levels.

One purpose for which the dyes were added to the control was to afford a visual discrimination between the various control ampuls. To agree with conventional acid base litmus color standards, a preferred color of the normal control would be yellow, for the acidosis the color control would be red, and for the alkalosis, the color control would be blue. Furthermore, the dye would also allow the clinician to determine visually, as with whole blood, whether or not air bubbles were present in the electrode chamber of the blood gas analyzer. Many of the conventional dye materials tested, however, were found either to be heat or light unstable and some appeared to catalyze an oxidation reaction so that the $P_{O_2}$ values became unstable.

The dyes finally selected as showing the greatest amount of stability within this liquid gas control system were F, D and C yellow, amaranth al lake, and alphazurine FG dyes. The yellow dye which is the trisodium salt of 5-oxo-1-(p-sulfophenyl)-4-[(p-sulfophenyl)azo]-2-pyrazoline-3-carboxylic acid, was found to be chemically stable in all levels of the standard. The amaranth dye was used to give the red color to the acidosis control. The alphazurine dye was used to yield the blue color in the alkalosis control.

Amaranth dye is known as F, D and C Red No. 2 and chemically as 3-hydroxy-4-[(4-sulfo-1-naphthaleny-1)azo]-2,7-napthalenedisulfonic acid; alphazurine is also known as C.I.F. Blue No. 2 or F, D, and C Blue No. 1 and is chemically N-ethyl-N-[4-[[4-[ethyl[(3-sulfophenyl)-methyl]amino]phenyl](2-sulfophenyl)methylene]-2,5-cyclohexediene-1-ylidene]-3-sulfobenzenemethanaminium hydroxide, inner salt, diammonium salt; F, D and C Yellow is also known as F, D and C Yellow No. 5 and chemically as 4,5-dihydro-5-oxo-1-(4-sulfophenyl)-4-[(4-sulfophenyl)azo]-1H-pyrazole-3-carboxylic acid, trisodium salt.

The following examples are given as the preferred embodiments for producing the three liquid controls of this invention:

EXAMPLE 1

Preparation of a liquid blood gas control containing normal values (pH=7.40, $P_{O_2}$=100, $P_{CO_2}$=40)

| Ingredients | For each 30 ml |
|---|---|
| 1. Water deionized | q.s. to 30 ml |
| 2. F, D & C yellow dye | 2 mg |
| 3. Triethanolamine | 447.6 mg |
| 4. Acetic Acid, glacial | q.s. |
| 5. Sodium Bicarbonate | 60.48 mg |
| 6. Gas Mixture: 13% $O_2$; 6.4% $CO_2$; Balance $N_2$ | |

Preparation
A. Filter 27 ml of Item No. 1 through a 0.22µ Millipore membrane.
B. Dissolve Items No. 2 and No. 3 in filtrate from Step A.
C. Bring Solution B to 37° C and adjust to pH 7.40 with Item No. 4. (See Note No. 1)
D. Cool Solution C to room temperature.
E. Dissolve Item No. 5 in Solution D and q.s. to 30 ml with Item No. 1.
F. Fill ampul with 1.7 ml of Solution from Step E. (See Note No. 2).
G. Flush filled ampul with Item No. 6.
H. Seal ampul.
I. Sterilize the ampul immediately in an autoclave.
J. Allow the solution to equilibrate with the gas in the sealed ampul for at least 72 hours before use.

Notes
1. An alternative procedure for large scale production can be used to obtain the target pH at 37° C. In this procedure, Steps C and D are eliminated and Item No. 5 is added at Step B.
The pH is then adjusted with Item No. 4 at room temperature to a value that will give the desired target value at 37° C. The proper room temperature pH value must be

EXAMPLE 1-continued determined empirically.
2. The fill solution prepared in Step E should be at room temperature (20°–23° C) before being dispensed into the ampules. The solution should be used within 30 minutes after preparation if it is not protected from the atmosphere. This is to prevent loss of carbon dioxide to the atmosphere.

EXAMPLE 2

Preparation of blood gas control containing acidosis values (pH=7.10, $Po_2$=150, $Pco_2$=20)

| Ingredients | For each 30 ml |
|---|---|
| 1. Water, deionized | q.s. to 30 ml |
| 2. Amaranth dye | 2 mg |
| 3. Triethanolamine | 447.6 mg |
| 4. Acetic acid, glacial | q.s. |
| 5. Sodium bicarbonate | 10.0 mg |
| 6. Gas mixture: 21.9% $O_2$; 6.09% $CO_2$; Balance $N_2$ | |

Preparation
The procedure is described in Example No. 1. In Step C, adjust to pH 7.10.

EXAMPLE 3

Preparation of a blood gas control containing alkalosis values (pH=7.60, $Po_2$=50, $Pco_2$=60)

| Ingredients | For each 30 ml |
|---|---|
| 1. Water, deionized | q.s. to 30 ml |
| 2. Alphazurine FG dye | 2 mg |
| 3. Triethanolamine | 447.6 mg |
| 4. Acetic acid, glacial | q.s. |
| 5. Sodium bicarbonate | 163.82 mg |
| 6. Gas Mixture: 6.6% $O_2$;6.75% $CO_2$; Balance $N_2$ | |

Preparation
The procedure is described in Example No. 1. In Step C, adjust to pH 7.60.

Example 1 represents the chemically normal pH, $Pco_2$, and respiratory function. In Example 2, the pH and $Pco_2$ values are representative of metabolic acidosis and the $Po_2$ is consistent with increased oxygen tension. The Example 3 control yields $Po_2$ values typical of hypoventilation or impaired diffusion.

The controls are made to be used directly in blood gas instruments by simply snapping off the neck of the ampuls and immediately aspirating or pumping the solution directly into the electrodechamber of the conventional blood gas instruments currently in service in medical laboratories.

I claim:

1. A liquid composition of matter for use as a blood gas control which comprises water, a dye, a buffering agent, a lower alkyl acid, a source of bicarbonate ion and an amount of dissolved oxygen, carbon dioxide and nitrogen gas.

2. The composition of claim 1 wherein the buffering agent is triethanolamine, wherein the acid is acetic acid, and wherein the source of bicarbonate is sodium bicarbonate.

3. The composition of claim 2 wherein the ratio of dye to triethanolamine to sodium bicarbonate is about 1 : 223.8 : 30.24.

4. The composition of claim 2 wherein the dye is F, D and C yellow dye.

5. The composition of claim 2 wherein the ratio of dye to triethanolamine to sodium bicarbonate is about 1 : 223.8 : 5.0.

6. The composition of claim 5 wherein the dye is selected from the group consisting of F, D and C yellow dye and amaranth dye.

7. The composition according to claim 2 wherein the ratio of dye to triethanolamine to sodium bicarbonate is about 1 : 223.8 : 81.91.

8. The method for preparing a liquid blood gas control which comprises:
Filtering a quantity of deionized water through a 0.22 $\mu$ filter membrane; Dissolving a quantity of a dye and triethanolamine in the filtered water;
Adjusting the solution so obtained to a pH range of about 7.1 to 7.6;
Dissolving a quantity of sodium bicarbonate in the pH adjusted solution;
Placing the solution so obtained in a glass ampul;
Flushing the ampul with a gas mixture comprising oxygen, carbon dioxide and nitrogen;
Sealing the ampul to effect an air tight seal; and
Sterilizing the ampul immediately after sealing in an autoclave.

9. A liquid composition or matter for use as a blood gas control which comprises water, a buffering agent, a lower alkyl acid, a source of bicarbonate ion and an amount of dissolved oxygen, carbon dioxide and nitrogen gas.

10. A composition of matter for use as a blood gas control which comprises water, triethanolamine acetic acid, sodium bicarbonate, and a gas mixture comprising oxygen in an amount of about 6.6 to about 21.9%, carbon dioxide in an amount of about 6.09 to about 6.75%, and nitrogen in an amount of about 71.35 to about 87.31%.

11. A composition of matter for use as a blood gas control which comprises water, F D, and C yellow dye, triethanolamine, sodium bicarbonate, acetic acid, an amount of dissolved gas comprising about 13% oxygen, about 6.4% carbon dioxide and about 80.6% nitrogen, and wherein the ratio of dye to triethanolamine to sodium bicarbonate is about 1 : 223.8 : 30.24 and wherein the pH of the composition is about 7.4.

12. A composition of matter for use as a blood gas control which comprises water, a dye selected from the group consisting of F D, and C yellow dye and E, D and C Red No. 2, triethanolamine, acetic acid, sodium bicarbonate, and an amount of dissolved gas comprising 21.9% oxygen, 6.09% carbon dioxide and 72.01% nitrogen, and wherein the ratio of dye to triethanolamine to sodium bicarbonate is about 1 : 223.8 : 5.0, and wherein the pH of the composition is about 7.1.

13. A composition of matter for use as a blood gas control which comprises water, a dye selected from the group consisting of F D, and C yellow dye and CIF Blue No. 2, triethanolamine, acetic acid, sodium bicarbonate, an amount of dissolved gas comprising about 6.6% oxygen, about 6.75% carbon dioxide and about 86.65% nitrogen, and wherein the ratio of dye to triethanolamine to sodium bicarbonate is about 1 :223.8 :81.91 and wherein the pH of the composition is about 7.6.

14. A package for use in containing a liquid composition having a predetermined pH, oxygen concentration and carbon dioxide concentration which comprises:
A sealed glass ampul wherein the seal is impermeable to air, and
A liquid composition of matter comprising water, a dye, triethanolamine, acetic acid, sodium bicarbonate and a predetermined concentration of oxygen, carbon dioxide, and nitrogen, and wherein said liquid concentration is sterile.

15. The composition of claim 1 wherein the dye is selected from the group of F, D and C Yellow No. 5 and CIF Blue No. 2.

16. The compound of claim 1 in which the dye is selected from the group consisting of F, D and C Yellow No. 5, F, D and C Red No. 2 and CIF Blue No. 2.

* * * * *

UNITED STATES PATENT OFFICE
CERTIFICATE OF CORRECTION

Patent No. 4,001,142  Dated January 4, 1977

Inventor(s) James E. Turner

It is certified that error appears in the above-identified patent and that said Letters Patent are hereby corrected as shown below:

Column 3, line 51, delete "tht" and insert --- that ---.

Claim 14, last line, delete "concentration" and insert --- composition ---.

Signed and Sealed this

Twelfth Day of December 1978

[SEAL]

Attest:

RUTH C. MASON
Attesting Officer

DONALD W. BANNER
Commissioner of Patents and Trademarks